United States Patent [19]
Ohashi et al.

[11] Patent Number: 5,529,910
[45] Date of Patent: Jun. 25, 1996

[54] METHOD FOR TESTING CAUSATIVE MICROORGANISMS OF FOOD POISONING AND REAGENTS THEREFOR

[75] Inventors: Tetsuo Ohashi; Hiroyuki Jikuya; Jun Takano, all of Kyoto; Yoshinari Shirasaki, Otsu; Hirohisa Abe, Kyoto; Koichi Yamagata, Osaka; Yoshihiro Aoyama, Kyoto; Jun Tada, Muko; Shigeru Fukushima, Otsu, all of Japan

[73] Assignee: Shimadzu Corporation, Kyoto, Japan

[21] Appl. No.: 126,754

[22] Filed: Sep. 27, 1993

Related U.S. Application Data

[63] Continuation of Ser. No. 944,755, Sep. 14, 1992, abandoned, which is a continuation of Ser. No. 553,083, Jul. 18, 1990, abandoned.

[30] Foreign Application Priority Data

| Jul. 18, 1989 | [JP] | Japan | 1-185683 |
| Jul. 18, 1989 | [JP] | Japan | 1-185685 |
| Sep. 27, 1989 | [JP] | Japan | 1-251400 |

[51] Int. Cl.$^6$ ............ C12P 19/34; C12N 1/00; C12N 15/00; C07H 21/04
[52] U.S. Cl. ............ 435/91.2; 435/6; 435/834; 435/842; 435/879; 536/23.1; 536/23.7; 536/24.33; 935/5; 935/8; 935/16; 935/76; 935/77; 935/78
[58] Field of Search ............ 435/6, 91, 172.3, 435/909, 842, 883, 849, 879, 824, 91.1, 91.2, 834, 842; 436/501, 811; 935/77, 78, 5, 8, 16, 76; 536/23.1, 23.7, 24.33

[56] References Cited

U.S. PATENT DOCUMENTS

| 4,683,202 | 7/1987 | Mullis | 435/91 |
| 4,994,368 | 2/1991 | Goodman et al. | 436/94 |

OTHER PUBLICATIONS

Wang et al., J. of Bact., Aug. 1985, pp. 487–492.
Biosis Abstract No. 77018727, Kreft et al., J. Bacteriol. 155(2), 1983, pp. 681–689.
Mezes et al., FEBS letters, 161(2), 1983, pp. 195–200.
Madgwick et al., Biochem. J. 248, 1987, pp. 657–662.
Sloma et al, Nucleic Acid Res. 11(14), 1983, pp. 4997–5004.
Biosis Abstract No.: 87049330, Zhao et al., Chin. J. Microbiol. Immunol. (Beijing) 8(3) 1988, 151–156.
Biosis Abstract No.: 85080168, Notermans et al., Appl. Environ Microbiol., 54(2), 1988, 531–533.
Medline Abstract No. 89186353, Bonventre et al., Rev. Infect. Dis. Jan.–Feb. 1989, 11 Suppl. pp. 590–595.
Biosis Subfile Abstract No. 89–28651, Romick et al., J. Food Prot., 52(7), 1989, pp. 466–470.
Tox Bib. Abstract No.–90–025098, Schuman et al., Appl. Environ. Microbiol., 55(9), 1989, pp. 24344–2348.
Biosis Abstract No. 87–24840, Davis, J. Food Prot., 50(6), 1987, pp. 487–489.
Biosis Abstract No. 87–09232, Hill et al., Plasmid, 16(3) 1986, p. 229.

*Primary Examiner*—W. Gary Jones
*Assistant Examiner*—Bradley L. Sisson
*Attorney, Agent, or Firm*—Foley & Lardner

[57] ABSTRACT

A method for testing causative bacterial species of food poisoning which is characterized by using two oligonucleotide primers that hybridize to opposite strands of bacterial DNA specifically, and flank a unique region in the target DNA and amplifying the specific fragment of the bacterial DNA, comprising the steps of:

(a) hybridizing the primer to specific gene sequence of bacteria in a sample, extending the hybridized primer with deoxynucleotide triphosphates (dATP, dCTP, dGTP, and dTTP), and resultantly making the double strand nucleotide;

(b) where the primer extension products are cleaved into each single strand of nucleotide by certain external force such as heat, pH and so on, one single strand functioning as a template for nucleotide extension with a primer of the other strand;

(c) repeating a series of cycles involving cleavage of primer extension products, primer hybridizing, extension of the hybridized primers to amplify the specific fragment of DNA, and detecting the amplified DNA fragment; and (d) as the result, determining whether or not the specific fragment is present in said sample, thereby to confirm a species of causative bacteria of food poisoning.

5 Claims, No Drawings

METHOD FOR TESTING CAUSATIVE MICROORGANISMS OF FOOD POISONING AND REAGENTS THEREFOR

This application is a continuation of U.S. application Ser. No. 07/944,755 filed Sep. 14, 1992 abandoned; which is a continuation of U.S. application Ser. No. 07/553,08, abandoned, filed Jul. 18, 1980.

BACKGROUND OF THE INVENTION

1. Field of the Invention

The present invention relates to detection of a species of causative bacteria of food poisoning in clinical tests or food tests.

2. Statement of the Prior Art

Where materials to be tested are patients' excreta or feces, food or wiping materials, operations of enrichment culture, separation culture, pure culture and then confirmation culture must be carried out, in order to identify that certain bacteria are causative bacteria of food poisoning. Since a time period required for each culture step is 18 to 24 hours, the required period becomes as long as about 4 days in total. In biochemical tests for confirmation culture, for example, egg-yolk reaction, VP reaction, gelatin liquefaction, starch hydrolysis, nitrate reduction and sugar reduction, etc. must be examined. Therefore, the biochemical tests are operationally complicated. Accompanied by the complicated operations, the biochemical tests are time consuming and expensive.

On the other hand, a DNA probing technique or hybridization technique using an oligonucleotide has been attempted in recent years. However, it is difficult to achieve satisfactory detection sensitivity and selectivity in such bacterial tests.

SUMMARY OF THE INVENTION

The present invention relates to detection of nucleic acids derived from a species of causative bacteria of food poisoning by a gene amplification technique in which an oligonucleotide functions as a primer for synthetic reaction of the nucleic acid. An object of the present invention is to provide a method for testing causative microorganisms of food poisoning in a simple and rapid way with high sensitivity.

DETAILED DESCRIPTION OF THE PREFERRED EMBODIMENTS

Herein, the gene amplification of the present invention is performed based on the polymerase chain reaction (hereafter simply referred to as PCR method; Science, 230, 1350 (1985)) developed by Saiki et al. According to this present invention method, where a specific nucleotide sequence region is to be detected, oligonucleotides are prepared that recognize ends of the region, one of the + chain and the other on the − chain to effect hybridization. The oligonucleotides are allowed to function as primers for template-dependent nucleotide polymerization of a nucleic acid test sample which is changed to a single stranded state by thermal denaturation or exposure to high pH, e.g., about 13 or higher. The resulting double stranded nucleic acid is again separated into a single strand and a similar reaction is again caused. By repeating this series of operations, the region inserted between the two primers is so amplified as to have a number of copies, whereby the region is detectable. The nucleotide sequence region of the primer varies depending upon the species of causative microorganisms of food poisoning. The following sequence regions correspond to the respective species:

*Bacillus cereus:*

| | |
|---|---|
| (5')d-GGTTTAAGTATTACAAGCC(3') | (a) |
| (5')d-GCATATACACCTAATCGAGC(3') | (b) |
| (5')d-CCACTAAGTCTTCTTTCG(3') | (c) |
| (5')d-TTCTGTATGCCCTTTCCCTG(3') | (d) |
| (5')d-ATTTCAGAAGCGCGTAACGG(3') | (e) |

*Vibrio parahaemolyticus:*

| | |
|---|---|
| (5')d-GGTAATGTGTATATCCAAC(3') | (f) |
| (5')d-CTACGTCAAAGTCGCACTAG(3') | (g) |

Salmonella:

| | |
|---|---|
| (5')d-GGCGAGCAGTTTGTCTGTC(3') | (h) |
| (5')d-TACCGCCATACGTCTGAGC(3') | (i) |
| (5')d-GTTTCGCCTGGCTGATACG(3') | (j) |

*Clostridium perfringens:*

| | |
|---|---|
| (5')d-AATACATATTGTCCTGCATC(3') | (k) |
| (5')d-GTAATAGATAAAGGAGATGG(3') | (l) |
| (5')d-GTAGTAGGATTTATACAAGC(3') | (m) |

*Staphylococcus aureus:*

| | |
|---|---|
| (5')d-CCAGATGAGTTGCACAAATCG(3') | (n) |
| (5')d-CACCAAATAGTGACGAGTTA(3') | (o) |

Enterotoxigenic *Escherichia coli* capable of producing heat-labile enterotoxin gene:

| | |
|---|---|
| (5')d-TTATCAATTTTGGTCTCGGTC(3') | (p) |
| (5')d-GAACTATGTTCGGAATATCG(3') | (q) |

*Campylobacter jejuni:*

| | |
|---|---|
| (5')d-AATAATCTGAATCCGATGGT(3') | (r) |
| (5')d-ATCAGACCATCACCCTTATC(3') | (s) |

Pathogenic *Escherichia coli* capable of producing heat-stable enterotoxin gene:

| | |
|---|---|
| (5')d-TAATAGCACCCGGTACAAGC(3') | (t) |
| (5')d-ATAAAAGTGGTCCTGAAAGC(3') | (u) |

*Salmonella typhimurium:*

| | |
|---|---|
| (5')d-GCGATACTCTTGTCGTCTGG(3') | (v) |
| (5')d-ATAGCTAATTGCTGCCGAGG(3') | (w) |

As a test sample, materials for clinical tests such as feces, urine, blood, tissue homogenate or the like and food materials may be used. To use these materials as test samples for gene amplification, an operation for releasing the nucleic acid component from bacteria present in the materials is required as a pretreatment. However, since more than several tens of molecules of nucleic acid hybridizable with the primer are present, a sample solution having nucleic acid in an amount sufficient to promote the gene amplification can be prepared merely by treating a test material with bacteriolysin, a surfactant, an alkali, etc. for a short period of time. The oligonucleotides having the sequences described above which are used as primers in the present invention are nucleic acid fragments having a size of more than 10 nucleotides, preferably more than 15 nucleotides, in view of their selectivity, detection sensitivity and reproducibility. The oligonucleotides may be either chemically synthesized or natural ones. The primers are not necessarily labeled especially for detection. The amplified sequence in a specific species of causative bacteria of food poisoning governed by the primer may be between 50 and 2000 nucleotides, desirably between 100 and 1000 nucleotides. For the template-dependent nucleotide polymerization, thermostable DNA polymerase is used. This enzyme may be derived from an organism of any source, so long as the enzyme can maintain its activity at a temperature of from 90° to 95° C. A temperature for thermal denaturation is between 90° and 95° C.; a temperature for annealing to hybridize the primer is between 37° and 65° C.; and a temperature for the polymerization is between 50° and 75° C. These procedures are made one cycle for gene amplification and gene amplification is carried out in 20 to 42 cycles to effect amplification. Detection is made by applying the enzyme reaction solution to agarose gel electrophoresis as it is, whereby the presence of the nucleic acid fragment amplified and its size can be confirmed. From the results, it can be judged if a nucleic acid having the sequence to be recognized by the primer is present in a test sample. This judgment also applies to the presence or absence of causative bacteria of food poisoning as it is. For detection of the amplified nucleic acid fragment, other electrophoresis or chromatography is also effective.

The oligonucleotides having the sequences (a) through (w) described above can selectively detect a specific gene sequence of a species of causative bacteria of food poisoning and hence can be used as reagents for tests. [Experiment 1: Detection of *Bacillus cereus*]

EXAMPLE 1

Preparation of test sample

Using 6 strains shown on the first row in Table 1 as *Bacillus cereus*, each strain was inoculated on an appropriate enrichment medium followed by culturing at 37° C. overnight under aerobic conditions. From 1.5 ml of the medium, cells were recovered by centrifugal operation. After washing once with 10 mM Tris-hydrochloride buffer (pH 7.5), the cells were suspended in 0.5 ml of a solution of 1 mg/ml of lysozyme in the buffer to cause bacteriolysis at 37° C. for 10 minutes. The same volume of phenol saturated with the above buffer was added to the bacteriolysis solution and the mixture was thoroughly agitated. After centrifugation, the supernatant was recovered and treated with ethanol to precipitate the nucleic acid component. The precipitate was dissolved in 1 ml of the above buffer and the resulting solution was used as a test sample.

Synthesis of primer

From the nucleotide sequences of β-lactamase I and II type genes for *Bacillus cereus* (Wang, W., et al.; J. Bacteriol., 163, 487–492 (1985); Hussain, M., et al.; J. Bacteriol., 164, 223–229 (1985)), the sequences (5')d-GGTTTAAGTATTACAAGCC(3')  (a)

(5')d-GCATATACACCTAATCGAGC(3')  (b)

(5')d-CCACTAAGTCTTCTTTCG(3')  (c)

(5')d-TTCTGTATGCCCTTTCCCTG(3')  (d)

(5')d-ATTTCAGAAGCGCGTAACGG(3')  (e)

were selected ((a), (b) and (c): from β-lactamase I type gene; (d) and (e) : from β-lactamase II type gene) and oligonucleotides having the same sequences were chemically synthesized. The chemical synthesis was carried out according to the triester method, using DNA synthesizer NS-1, manufactured by Shimadzu Corporation. The synthesized oligonucleotide fragment was purified using C18 reverse phase column.

Gene amplification

Using 3 µl of the sample solution described above, 16.05 µl of sterile distilled water, 3 µl of buffer for 10-fold reaction, 4.8 µl of dNTP solution, 1.5 µl of primer (1), 1.5 µl of primer (2) and 0.15 µl of thermostable DNA polymerase were added to the sample solution to prepare 30 µl of the reaction solution. To a container charged with the reaction solution, 50 µl of mineral oil (manufactured by SIGMA Co.) was added to form a layer on the reaction solution. The content of each liquid added is shown below.

Buffer for 10-fold reaction: 500 mM KCl, 100 mM Tris-HCl (pH 8.3), 15 mM $MgCl_2$, 0.1% (w/v) gelatin dNTP solution: a mixture of dATP, dCTP, dGTP and dTTP in the final concentration of 1.25 mM each Primers (1) and (2): an aqueous solution of each of the chemically synthesized and purified products (5 ODU/ml)

As the primers, the following combinations were chosen from the sequences ((a) through (e)) shown above and used.

| Primer (1) + Primer (2) |
| --- |
| (a) + (b) |
| (a) + (c) |
| (d) + (e) |

Thermostable DNA polymerase: Taq DNA polymerase (5 units/ml; manufactured by Perkin Elmer Cetus Co.)

The reaction conditions are as follows:
Thermal denaturation: 94° C., 1 minute
Annealing: 37 ° C., 1 minute
Polymerization: 60° C., 1 minute The procedure from the thermal denaturation to the polymerization via annealing was made one cycle (time required: 5.7 minutes) and 42 cycles of the procedure were repeated (total time required: about 4 hours). These operations were carried out by programming the reaction conditions described above on DNA Thermal Cycler manufactured by Perkin Elmer Cetus Co., Ltd.

Detection

In order to detect the amplified nucleotide fragment from the reaction solution, agarose gel electrophoresis was performed as follows.

Agarose gel was used in a gel concentration of 2% (w/v). Agarose gel used contained ethidium bromide (0.5 µg/ml ). The electrophoresis was carried out under electric conditions of 100 V in constant voltage for 30 minutes. The procedures and other conditions were the same as those described in Maniatis et al.; Molecular Cloning (1982). In addition to electrophoresis of the reaction solution, a molecular weight marker was also subjected to electrophoresis at the same time. By comparison in relative mobility, the size of the nucleotide fragment in the gel detected by ultraviolet rays, etc. was calculated.

Results

As described above, the nucleotide sequences of both types I and II of β-lactamase gene were already determined. Therefore, the size of nucleotides amplified by the oligonucleotides of the present invention, namely, the primers, through gene amplification can be deduced. According to the deduction, the sizes of 156 nucleotides, 313 nucleotides and 232 nucleotides are to be amplified in primers (a) and (b), (a) and (c) and (d) and (e), respectively. The numerical values shown in Table 1 show the results obtained by measuring the size of nucleotides amplified by the method described above, wherein the unit is a killo base pair. As is understood from the table, the respective combinations of the primers show numerical values identical with the deduced sizes of nucleotides, indicating that the region targeted by the β-lactamase gene is correctly amplified.

TABLE 1

| Strain | Combination of Primer | | |
|---|---|---|---|
| | (a) + (b) | (a) + (c) | (d) + (e) |
| Bacillus cereus (1) | 0.15 | 0.31 | 0.23 |
| Bacillus cereus (2) | 0.15 | 0.31 | 0.23 |
| Bacillus cereus (3) | 0.15 | 0.31 | 0.23 |
| Bacillus cereus (4) | 0.15 | 0.31 | 0.23 |
| Bacillus cereus (5) | 0.15 | 0.31 | 0.23 |
| Bacillus cereus (6) | 0.15 | 0.31 | 0.23 |

Strain numbers (1) through (6) of Bacillus cereus and organizations from which the strains were acquired are shown below.
(1) JCM 2152: Research Institute of Science and Chemistry
(2) ATCC 33018: American Type Culture Collection
(3) ATCC 33019: "
(4) ATCC 11778: "
(5) ATCC 14579: "
(6) ATCC 27348: "

EXAMPLE 2

In order to confirm as to if the results obtained in Example 1 are selective to *Bacillus cereus*, the results were compared and studied with other species than *Bacillus cereus* that could be tested in clinical tests.

The same method as shown in Example 1 was used but with respect to strains (3) and (7), incubation was performed at 37° C. overnight under anaerobic conditions to prepare test samples applicable to the gene amplification method. The strains cultured to prepare test samples are 7 species shown on the first row of Table 2. Human placental DNA was prepared in a concentration of 1 μg/ml and was also subjected to the gene amplification in a similar manner. The results are shown in Table 2. As in Table 1, the unit of numerical values in the column is a killo base pair. In a part of the bacterial species, the amplified nucleotide fragments considered to be the by-products in gene amplification were detected but each of them has a size different from that of the nucleotide fragment deduced from the nucleotide sequence of β-lactamase gene. If these bacteria have the same β-lactamase gene as that of *Bacillus cereus*, the nucleotide fragment having the same size as the results of Example 1 must be detected. Accordingly, it is evident that the amplified nucleotides derived from these bacteria are not formed by recognizing β-lactamase gene and can thus be readily distinguished over and detected distinctly from *Bacillus cereus*. By performing agarose gel electrophoresis applied to the examples of the present invention under the aforesaid conditions, differences in size of nucleotides having 5 to 10 base pairs can be distinguished within the range below 100 base pairs and differences in size of nucleotides having 10 to 20 base pairs can be distinguished within the range of from 100 to 500 base pairs. Furthermore, by increasing the accuracy of measurement in size of nucleotide using acrylamide, etc. as gel, reliability in the selective detection is considered to be more enhanced.

TABLE 2

| Strain | Combination of Primer | | |
|---|---|---|---|
| | (a) + (b) | (a) + (c) | (d) + (e) |
| Bacillus cereus (JCM 2152) | 0.15 | 0.31 | 0.23 |
| Bacillus subtilis (1) | — | — | — |
| Salmonella typhimurium (2) | 0.18 | — | 0.18 |
| Campylobacter jejuni (3) | 0.20 | — | — |
| Escherichia coli (4) | — | — | 0.18 |
| Staphylococcus aureus (5) | — | 1.00 | 0.40 |
| Vibrio parahaemolyticus (6) | 0.33 | — | 0.70 |
| Clostridium perfringens (7) | — | — | — |
| Human placenta (8) | 0.28 | — | — |

Strain numbers (1) through (8) and organizations from which the strains were acquired are shown below.
(1) JCM 1465: Research Institute of Science and Chemistry
(3) JCM 2013: "
(4) JCM 1649: "
(5) JCM 2413: "
(7) JCM 3816: "
(2) IFO 12529: Research Institute of Fermentation
(6) IFO 12711: "
(8) Human placental DNA: manufactured by Onco Co., Ltd.

EXAMPLE 3

It is shown below up to what trace amount *Bacillus cereus* in the test sample could be detected according to the method of the present invention.

Method

*Bacillus cereus* (JCM 2152) was inoculated on 100 ml of enrichment medium followed by culturing at 37° C. overnight under aerobic conditions. From the medium, cells were recovered by centrifugal operation. After washing once with 10 mM Tris-hydrochloride buffer (pH 7.5), the cells were suspended in 20 ml of lysozyme solution (1 mg/ml) in the buffer to cause bacteriolysis at 37° C. for 10 minutes. To the lysed solution was added 1 ml of 20% (w/v) SDS aqueous solution and the mixture was heated at the same temperature for 10 minutes. Then proteinase K was added thereto in a final concentration of 750 μg/ml followed by heating for further 30 minutes. The same volume of phenol saturated (with the above buffer) was added to the reaction mixture. After thoroughly agitating, the supernatant was recovered by centrifugation. Swine pancrease ribonuclease was added to the solution in a final concentration of 50 μg/ml followed by heating at 37° C. for 60 minutes.

The same volume of phenol described above was added to the solution. After thoroughly agitating, the supernatant was recovered by centrifugation. For ethanol precipitation, 3M sodium acetate buffer (pH 5.2) in a volume of 1/10 that of the recovered solution was added to and mixed with the supernatant. Then ethanol was added to the mixture in a volume of twice that of the recovered solution followed by agitation. The precipitated thread-like DNA was recovered by centrifugal operation and again dissolved in 10 ml of 10 mM Tris-HCl (pH 7.5) buffer to obtain pure DNA standard. An amount of DNA in the standard was calculated based on its absorbance at a wavelength of 260 nm.

One microgram of chromosomal DNA of *Bacillus cereus* corresponds to $3\times10^8$ *Bacillus cereus*. Thus, if how many numbers of *Bacillus cereus* are present, they can be detected by the amount of DNA incorporated into the gene amplification system. Gene amplification and other procedures are as shown in Example 1. As the combination of primers, (a)+(c) was used. Detection of the amplified nucleotide fragment was made by taking a picture of the electrophoresed gel on a transilluminator and confirming the band on a film. As a camera, Mamiya RB67 was used and a film was Polaroid type 667. Conditions for taking the picture: focus, 5.6; shutter speed, 1 second; Kenko RI filter was used.

Results

The results are presented below.

| Lane No. | Amount of DNA (g) | Number of Molecule |
|---|---|---|
| (1) | $10^{-3}$ | $3 \times 10^5$ |
| (2) | $10^{-4}$ | $3 \times 10^4$ |
| (3) | $10^{-5}$ | $3 \times 10^3$ |
| (4) | $10^{-6}$ | $3 \times 10^2$ |
| (5) | $10^{-7}$ | $3 \times 10^1$ |
| (6) | $10^{-8}$ | $3 \times 10^0$ |
| (7) | $10^{-9}$ | $3 \times 10^{-1}$ |

The desired band was confirmed also in Lane No. (5). But the desired band was not confirmed in Lane No. (6) and (7). This indicates than an amount of DNA corresponding to 30 molecules of chromosomal DNA of *Bacillus cereus* as detected. Theoretically, 30 pieces of *Bacillus cereus* are sufficient for the detection.

[Experiment 2: Detection of *Vibrio parahaemolyticus*]

EXAMPLE 1

Preparation of test sample

Using 5 strains shown on the first row in Table 3 as *Vibrio parahaemolyticus*, each strain was inoculated on an appropriate enrichment medium followed by culturing at 37° C. overnight under aerobic conditions. From 1.5 ml of the medium, cells were recovered by centrifugal operation. After washing once with 10 mM Tris-hydrochloride buffer (pH 7.5), the cells were suspended in 0.5 ml of a solution of 1 mg/ml of lysozyme in the buffer to cause bacteriolysis at 37° C. for 10 minutes. The same volume of phenol saturated with the above buffer was added to the bacteriolysis solution and the mixture was thoroughly agitated. After centrifugation, the supernatant was recovered and treated with ethanol to precipitate the nucleic acid component. The precipitate was dissolved in 1 ml of the above buffer and the resulting solution was used as a test sample.

Synthesis of primer

From the nucleotide sequences of the gene for *Vibrio parahaemolyticus* (Nishibuchi, M. and Kaper, J. B.; J. Bacteriol., 162, 558–564 (1985)), the sequences (5')d-GGTAATGTGTATATCCAAC(3')  (a)

(5')d-CTACGTCAAAGTCGCACTAG(3')  (b)

were selected and oligonucleotides having the same sequences were chemically synthesized. The chemical synthesis was carried out according to the triester method, using DNA synthesizer NS-1, manufactured by Shimadzu Corporation Ltd. The synthesized oligonucleotide fragment was purified using C18 reverse phase column.

Gene amplification

Using 3 µl of the sample solution described above, 16.05 µl of sterile distilled water, 3 µl of buffer for 10-fold reaction, 4.8 µl of dNTP solution, 1.5 µl of primer (1), 1.5 µl of primer (2) and 0.15 µl of thermostable DNA polymerase were added to the sample solution to prepare 30 µl of the reaction solution. To a container charged with the reaction solution, 50 µl of mineral oil (manufactured by SIGMA Co.) was added to form a layer on the reaction solution. The content of each liquid added is shown below.

Buffer for 10-fold reaction: 500 mM KCl, 100 mM Tris-HCl (pH 8.3), 15 mM $MgCl_2$, 0.1% (w/v) gelatin dNTP solution: a mixture of dATP, dCTP, dGTP and dTTP in the final concentration of 1.25 mM each Primers (1) and (2): an aqueous solution of each of the chemically synthesized and purified products (5 ODU/ml)

Thermostable DNA polymerase: Taq DNA polymerase (5 units/ml; manufactured by Perkin Elmer Cetus Co. )

The reaction conditions are as follows:

Thermal denaturation: 94° C., 1 minute

Annealing: 37° C., 1 minute

Polymerization: 60° C., 1 minute

The procedure from the thermal denaturation to the polymerization via annealing was made one cycle (time required: 5.7 minutes) and 42 cycles of the procedure were repeated (total time required: about 4 hours). These operations were carried out by programming the reaction conditions described above on DNA Thermal Cycler manufactured by Perkin Elmer Cetus Co., Ltd.

Detection

In order to detect the amplified nucleotide fragment from the reaction solution, agarose gel electrophoresis was performed as follows.

Agarose gel was used in a gel concentration of 2% (w/v). Agarose gel used contained ethidium bromide (0.5 µg/ml ). The electrophoresis was carried out under electric conditions of 100 V in constant voltage for 30 minutes. The procedures and other conditions were the same as those described in Maniatis et al.; Molecular Cloning (1982). In addition to electrophoresis of the reaction solution, a molecular weight marker was also subjected to electrophoresis at the same time. By comparison in relative mobility, the size of nucleotide the fragment was calculated.

Results

As described above, the nucleotide sequences of tdh gene of *Vibrio parahaemolyticus* were already determined. Therefore, the size of nucleotides amplified by the oligonucleotides of the present invention, namely, the primers, through gene amplification can be deduced. According to the deduction, the size of 439 nucleotides is to be amplified in primers (a) and (b). The numerical values shown in Table 3 show the results obtained by measuring the size of nucleotides amplified by the method described above, wherein the unit is a killo base pair. As is understood from the table, the respective combinations of the primers show numerical values identical with the deduced sizes of nucleotides, indicating that the region targeted by tdh gene is correctly amplified.

TABLE 3

| Strain | Combination of Primer (a) + (b) |
|---|---|
| *Vibrio parahaemolyticus* (1) | 0.44 |
| *Vibrio parahaemolyticus* (2) | 0.44 |

TABLE 3-continued

| Strain | Combination of Primer (a) + (b) |
|---|---|
| Vibrio parahaemolyticus (3) | 0.44 |
| Vibrio parahaemolyticus (4) | 0.44 |
| Vibrio parahaemolyticus (5) | 0.44 |

Strain numbers (1) through (5) of Vibrio parahaemolyticus and organizations from which the strains were acquired are shown below.
(1) IFO 12711: Research Institute of Fermentation
(2) ATCC 17803: American Type Culture Collection
(3) ATCC 27519: "
(4) ATCC 27969: "
(5) ATCC 33844: "

EXAMPLE 2

In order to confirm as to if the results obtained in Example 1 are selective to Vibrio parahaemolyticus, the results were compared and studied with other species than Vibrio parahaemolyticus that could be tested in clinical tests.

The same method as shown in Example 1 was used but with respect to strains (13), (14) and (15), incubation was performed at 37° C. overnight under anaerobic conditions to prepare test samples applicable to the gene amplification method. The strains cultured to prepare test samples are 16 species shown on the first row of Table 4. Human placental DNA was prepared in a concentration of 1 μg/ml and was also subjected to the gene amplification in a similar manner.

The results are shown in Table 4. As in Table 3, the unit of numerical values in the column is a killo base pair. In a part of the bacterial species, the amplified nucleotide fragments considered to be the by-products in gene amplification were detected, but each of them has a size different from that of the nucleotide fragment deduced from the nucleotide sequence of tdh gene. If these bacteria have the same tdh gene as that of Vibrio parahaemolyticus, the nucleotide fragment having the same size as the results of Example 1 must be detected. Accordingly, it is evident that the amplified nucleotides derived from these bacteria are not formed by recognizing tdh gene and can thus be readily distinguished over and detected distinctly from Vibrio parahaemolyticus. By performing agarose gel electrophoresis applied to the examples of the present invention under the aforesaid conditions, differences in size of nucleotide having 5 to 10 base pairs can be distinguished within the range below 100 base pairs and differences in size of nucleotide having 10 to 20 base pairs can be distinguished within the range of from 100 to 500 base pairs. Furthermore, by increasing the accuracy of measurement in size of nucleotide using acrylamide, etc. as gel, reliability in the selective detection is considered to be more enhanced.

TABLE 4

| Strain | Combination of Primer (a) + (b) |
|---|---|
| Vibrio parahaemolyticus (IFO 12711) | 0.44 |
| Vibrio mimicus (1) | 0.08 |
| Vibrio anguillarum (2) | 0.35 |
| Vibrio anguillarum (3) | 0.35 |
| Vibrio fluvialis (4) | — |
| Vibrio hollisae (5) | 0.35 |
| Vibrio cholerae (6) | 0.20 |
| Vibrio cholerae (7) | 0.32 |
| Vibrio cholerae (8) | — |
| Bacillus cereus (9) | — |

TABLE 4-continued

| Strain | Combination of Primer (a) + (b) |
|---|---|
| Salmonella typhimurium (10) | 0.65 |
| Staphylococcus aureus (11) | 1.00 |
| Escherichia coli (12) | — |
| Campylobacter jejuni (13) | |
| Clostridium perfringens (14) | — |
| Yersinia enterocolitica (16) | 0.20 |
| Human placenta (17) | — |

Strain numbers (1) through (17) of Vibrio parahaemolyticus and organizations from which the strains were acquired are shown below.
(2) IFO 12710: Research Institute of Fermentation
(3) IFO 13266: "
(10) IFO 12529: "
(1) ATCC 33658: American Type Culture Collection
(6) ATCC 25872: "
(7) ATCC 9458: "
(8) ATCC 9459: "
(14) ATCC 12917: "
(16) ATCC 9610: "
(4) JCM 3752: Research Institute of Science and Chemistry
(5) JCM 1283: "
(9) JCM 2152: "
(11) JCM 2413: "
(12) JCM 1649: "
(13) JCM 2013: "
(15) JCM 5826: "
(17) Human placental DNA: manufactured by Onco Co., Ltd.

[Experiment 3: Detection of Salmonella]

EXAMPLE 1

Preparation of test sample

Using 14 strains of 7 species shown on the first row in Table 5 as Salmonella, each strain was inoculated on an appropriate enrichment medium followed by culturing at 37° C. overnight under aerobic conditions. From 1.5 ml of the medium, cells were recovered by centrifugal operation. After washing once with 10 mM Tris-hydrochloride buffer (pH 7.5), the cells were suspended in 0.5 ml of a solution of 1 mg/ml of lysozyme in the buffer to cause bacteriolysis at 37° C. for 10 minutes. The same volume of phenol saturated with the above buffer was added to the bacteriolysis solution and the mixture was thoroughly agitated. After centrifugation, the supernatant was recovered and treated with ethanol to precipitate the nucleic acid component. The precipitate was dissolved in 1 ml of the above buffer and the resulting solution was used as a test sample.

Synthesis of primer

From the nucleotide sequences of ara C gene for Salmonella (Clarke, P., et al.; Gene, 18, 157–163 (1982)), the sequences (5')d-GGCGAGCAGTTTGTCTGTC(3')     (a)

(5')d-TACCGCCATACGTCTGAGC(3')     (b)

(5')d-GTTTCGCCTGGCTGATACG(3')     (c)

were selected and oligonucleotides having the same sequences were chemically synthesized. The chemical synthesis was carried out according to the triester method, using DNA synthesizer, NS-1, manufactured by Shimadzu Corporation Ltd. The synthesized oligonucleotide fragment was purified using C18 reverse phase column.

Gene amplification

Using 3 μl of the sample solution described above, 16.05 μl of sterile distilled water, 3 μl of buffer for 10-fold reaction, 4.8 μl of dNTP solution, 1.5 μl of primer (1), 1.5 μl of primer (2) and 0.15 μl of thermostable DNA polymerase were added to the sample solution to prepare 30 μl of the reaction solution. To a container charged with the reaction solution, 50 μl of mineral oil (manufactured by SIGMA Co.) was added to form a layer on the reaction solution. The content of each liquid added is shown below.

Buffer for 10-fold reaction: 500 mM KCl, 100 mM Tris-HCl (pH 8.3), 15 mM $MgCl_2$, 0.1% (w/v) gelatin dNTP solution: a mixture of dATP, dCTP, dGTP and dTTP in the final concentration of 1.25 mM each Primers (1) and (2): an aqueous solution of each of the chemically synthesized and purified products (5 ODU/ml)

As the primers, the following combinations were chosen from the sequences ((a) through (c)) shown in above and used.

| Primer (1) + Primer (2) |
| --- |
| (a) + (b) |
| (a) + (c) |

Thermostable DNA polymerase: Taq DNA polymerase (5 units/ml; manufactured by Perkin Elmer Cetus Co.)

The reaction conditions are as follows:
Thermal denaturation: 94° C., 1 minute
Annealing: 37° C., 1 minute
Polymerization: 60° C., 1 minute The procedure from the thermal denaturation to the polymerization via annealing was made one cycle (time required: 5.7 minutes) and 42 cycles of the procedure were repeated (total time required: about 4 hours). These operations were carried out by programming the reaction conditions described above on DNA Thermal Cycler manufactured by Perkin Elmer Cetus Co., Ltd.

Detection

In order to detect the amplified nucleotide fragment from the reaction solution, agarose gel electrophoresis was performed as follows.

Agarose gel was used in a gel concentration of 2% (w/v). Agarose gel used contained ethidium bromide (0.5 μg/ml). The electrophoresis was carried out under electric conditions of 100 V in constant voltage for 30 minutes. The procedures and other conditions were the same as those described in Maniatis et al.; Molecular Cloning (1982). In addition to electrophoresis of the reaction solution, a molecular weight marker was also subjected to electrophoresis at the same time. By comparison in relative mobility, the size of the nucleotide fragment was calculated.

Results

As described above, the nucleotide sequence of ara C gene was already determined. Therefore, the size of nucleotides amplified by the oligonucleotides of the present invention, namely, the primers, through gene amplification can be deduced. According to the deduction, the sizes of 329 nucleotides and 539 nucleotides are to be amplified in primers (a) and (b) and (a) and (c), respectively. The numerical values shown in Table 5 show the results obtained by measuring the size of nucleotides amplified by the method described above, wherein each unit is a killo base pair. As is understood from the table, the respective combinations of the primers show numerical values identical with the deduced sizes of nucleotides, indicating that the region targeted by ara C gene is correctly amplified.

TABLE 5

| Strain | Combination of Primer | |
| --- | --- | --- |
| | (a) + (b) | (a) + (c) |
| Salmonella typhimurium (1) | 0.33 | 0.54 |
| Salmonella typhimurium (2) | 0.33 | 0.54 |
| Salmonella typhimurium (3) | 0.33 | 0.54 |
| Salmonella typhimurium (4) | 0.33 | 0.54 |
| Salmonella typhimurium (5) | 0.33 | 0.54 |
| Salmonella typhimurium (6) | 0.33 | 0.54 |
| Salmonella typhimurium (7) | 0.33 | 0.54 |
| Salmonella typhimurium (8) | 0.33 | 0.54 |
| Salmonella enteritidis (9) | 0.33 | 0.54 |
| Salmonella gallinarum (10) | 0.33 | 0.54 |
| Salmonella blockley (11) | 0.33 | 0.54 |
| Salmonella derby (12) | 0.33 | 0.54 |
| Salmonella infantis (13) | 0.33 | 0.54 |
| Salmonella montevideo (14) | 0.33 | 0.54 |

Strain numbers (1) through (14) of Salmonella and organizations from which the strains were acquired are shown below.
(1) IFO 12529: Research Institute of Fermentaion
(2) IFO 13245: "
(3) IFO 14193: "
(4) IFO 14194: "
(5) IFO 14209: "
(6) IFO 14210: "
(7) IFO 14211: "
(8) IFO 14212: "
(9) IFO 3313: "
(10) IFO 3163: "
(11) NIAH 1197: National Institute of Animal Health of the Ministry of Agriculture, Forestry and Fisheries
(12) NIAH 1199: National Institute of Animal Health of the Ministry of Agriculture, Forestry and Fisheries
(13) NIAH 1218: National Institute of Animal Health of the Ministry of Agriculture, Forestry and Fisheries
(14) NIAH 1211: National Institute of Animal Health of the Ministry of Agriculture, Forestry and Fisheries

EXAMPLE 2

In order to confirm as to if the results obtained in Example 1 are selective to Salmonella, the results were compared and studied with other species than Salmonella that could be tested in clinical tests.

The same method as shown in Example 1 was used but with respect to strains (2), (6) and (18), incubation was performed at 40° C. overnight under anaerobic conditions to prepare test samples applicable to the gene amplification method. The strains cultured to prepare test samples are 11 species shown on the first row of Table 6. Human placental DNA was prepared in a concentration of 1 μg/ml and was also subjected to the gene amplification in a similar manner.

The results are shown in Table 6. As in Table 5, the unit of numerical values in the column is a killo base pair. In a part of the bacterial species, the amplified nucleotide fragments considered to be the by-products in gene amplification were detected but each of them has a size different from that of the nucleotide fragment deduced from the nucleotide sequence of ara C gene. If these bacteria have the same ara C gene as that of Salmonella, the nucleotide fragment having the same size as the results of Example 1 must be detected. Accordingly, it is evident that the amplified nucleotides derived from these bacteria are not formed by recognizing ara C gene and can thus be readily distinguished over and detected distinctly from Salmonella. By performing agarose gel electrophoresis applied to the examples of the present invention under the aforesaid conditions, differences in size of nucleotides having 5 to 10 base pairs can be distinguished within the range below 100 base pairs and differences in size of nucleotides having 10 to 20 base pairs can be distinguished within the range of from 100 to 500 base pairs. Furthermore, by increasing the accuracy of measurement in size of nucleotide using acrylamide, etc. as gel, reliability in the selective detection is considered to be more enhanced.

TABLE 6

| Strain | Combination of Primer | |
|---|---|---|
| | (a) + (b) | (a) + (c) |
| Salmonella typhimurium (IFO 12529) | 0.33 | 0.54 |
| Bacillus cereus (9) | 0.20 | 0.20 |
| Campylobacter jejuni (2) | — | — |
| Escherichia coli (3) | 0.50 | 0.40 |
| Vibrio pharahaemolyticus (4) | 0.50 | 0.20 |
| Staphylococcus aureus (5) | 0.10 | 0.20 |
| Clostridium perfringens (6) | — | — |
| Shigella dysenteriae (7) | 0.80 | — |
| Shigella flexneri (8) | 0.50 | — |
| Shigella sonnei (9) | 0.80 | 0.30 |
| Yersinia enterocolitica (10) | 0.20 | — |
| Bacteroides vulgatus (11) | — | — |
| Human placenta (12) | 0.20 | — |

(1) JCM 2152: Research Institute of Science and Chemistry
(2) JCM 2013: "
(3) JCM 1469: "
(5) JCM 2413: "
(6) JCM 3816: "
(11) JCM 5826: "
(4) IFO 12711: Research Institute of Fermentation
(7) ATCC 9361: American Type Culture Collection
(8) ATCC 29903: "
(9) ATCC 29930: "
(10) ATCC 9610: "
(12) Human placental DNA: manufactured by Onco Co., Ltd.

[Experiment 4: Detection of *Clostridium perfringens*]

EXAMPLE 1

Preparation of test sample

Using 11 strains shown on the first row in Table 7 as *Clostridium perfringens*, each strain was inoculated on an appropriate enrichment medium followed by culturing at 40° C. overnight under anaerobic conditions. From 1.5 ml of the medium, cells were recovered by centrifugal operation. After washing once with 10 mM Tris-hydrochloride buffer (pH 7.5), the cells were suspended in 0.5 ml of a solution of 1 mg/ml of lysozyme in the buffer to cause bacteriolysis at 37° C. for 10 minutes. The same volume of phenol saturated with the above buffer was added to the bacteriolysis solution and the mixture was thoroughly agitated. After centrifugation, the supernatant was recovered and treated with ethanol to precipitate the nucleic acid component. The precipitate was dissolved in 1 ml of the above buffer and the resulting solution was used as a test sample.

Synthesis of primer

As information on the nucleotide sequence of enterotoxin gene for *Clostridium perfringens*, information obtained by reverse translation from the amino acid sequence of enterotoxin (Richardson M. and Granum, P. E.; FEBS Letters, 182, 479–484 (1985)) was used. The sequences (5')d-AATACATATTGTCCTGCATC(3')     (a)

(5')d-GTAATAGATAAAGGAGATGG(3')    (b)

(5')d-GTAGTAGGATTTATACAAGC(3')    (c)

were selected and oligonucleotides having the same sequences were chemically synthesized. The chemical synthesis was carried out according to the triester method, using DNA synthesizer NS-1, manufactured by Shimadzu Corporation Ltd. The synthesized oligonucleotide fragment was purified using C18 reverse phase column.

Gene amplification

Using 3 µl of the sample solution described above, 16.05 µl of sterile distilled water, 3 µl of buffer for 10-fold reaction, 4.8 µl of dNTP solution, 1.5 µl of primer (1), 1.5 µl of primer (2) and 0.15 µl of thermostable DNA polymerase were added to the sample solution to prepare 30 µl of the reaction solution. To a container charged with the reaction solution, 50 µl of mineral oil (manufactured by SIGMA Co.) was added to form a layer on the reaction solution. The content of each liquid added is shown below.

Buffer for 10-fold reaction: 500 mM KCl, 100 mM Tris-HCl (pH 8.3), 15 mM $MgCl_2$, 0.1% (w/v) gelatin dNTP solution: a mixture of dATP, dCTP, dGTP and dTTP in the final concentration of 1.25 mM each Primers (1) and (2): an aqueous solution of each of the chemically synthesized and purified products (5 ODU/ml)

As the primers, the following combinations were chosen from the sequences ((a) through (c)) shown above and used.

| Primer (1) + Primer (2) |
|---|
| (a) + (b) |
| (a) + (c) |

Thermostable DNA polymerase: Taq DNA polymerase (5 units/ml; manufactured by Perkin Elmer Cetus Co.)

The reaction conditions are as follows:
Thermal denaturation: 94° C., 1 minute
Annealing: 37° C., 1 minute
Polymerization: 60° C., 1 minute The procedure from the thermal denaturation to the polymerization via annealing was made one cycle (time required: 5.7 minutes) and 42 cycles of the procedure were repeated (total time required: about 4 hours). These operations were carried out by programming the reaction conditions described above on DNA Thermal Cycler manufactured by Perkin Elmer Cetus Co., Ltd.

Detection

In order to detect the amplified nucleotide fragment from the reaction solution, agarose gel electrophoresis was performed as follows.

Agarose gel was used in a gel concentration of 2% (w/v). Agarose gel used contained ethidium bromide (0.5 µg/ml). The electrophoresis was carried out under electric conditions of 100 V in constant voltage for 30 minutes. The procedures and other conditions were the same as those described in Maniatis et al.; Molecular Cloning (1982). In addition to electrophoresis of the reaction solution, a molecular weight marker was also subjected to electrophoresis at the same time. By comparison in relative mobility, the size of the nucleotide fragment was calculated.

Results

As described above, the size of nucleotides amplified by the oligonucleotides of the present invention, namely, the primers, through gene amplification can be deduced from the nucleotide sequence of enterotoxin gene of *Clostridium perfringens*. According to the deduction, the sizes of 728 nucleotides and 602 nucleotides are to be amplified in primers (a) and (b) and (a) and (c), respectively. The numerical values shown in Table 7 show the results obtained by measuring the size of nucleotides amplified by the method described above, wherein the unit is a killo base pair. As is understood from the table, the respective combinations of the primers show numerical values identical with the deduced sizes of nucleotides except for strains (5), (7) and (11), indicating that the region targeted by enterotoxin gene is correctly amplified.

TABLE 7

| Strain | Combination of Primer | |
|---|---|---|
|  | (a) + (b) | (a) + (c) |
| *Clostridium perfringens* (1) | 0.73 | 0.60 |
| *Clostridium perfringens* (2) | 0.73 | 0.60 |
| *Clostridium perfringens* (3) | 0.73 | 0.60 |
| *Clostridium perfringens* (4) | 0.73 | 0.60 |
| *Clostridium perfringens* (5) | — | — |
| *Clostridium perfringens* (6) | 0.73 | 0.60 |
| *Clostridium perfringens* (7) | — | — |
| *Clostridium perfringens* (8) | 0.73 | 0.60 |
| *Clostridium perfringens* (9) | 0.73 | 0.60 |
| *Clostridium perfringens* (10) | 0.73 | 0.60 |
| *Clostridium perfringens* (11) | 0.30 | — |

Strain numbers (1) through (11) of *Clostridium perfringens* and organizations from which the strains were acquired are shown below.
(1) ATCC 12915: American Type Culture Collection
(2) ATCC 12916: "
(3) ATCC 12917: "
(4) ATCC 12918: "
(5) ATCC 12919: "
(6) ATCC 12920: "
(7) ATCC 12921: "
(8) ATCC 12922: "
(9) ATCC 12924: "
(10) ATCC 12925: "
(11) JCM 3816: Research Institute of Science and Chemistry

EXAMPLE 2

In order to confirm as to if the results obtained in Example 1 are selective to *Clostridium perfringens*, the results were compared and studied with other species than *Clostridium perfringens* that could be tested in clinical tests.

The same method as shown in Example 1 was used but with respect to strains (6), (7) and (9), incubation was performed at 40° C. overnight under anaerobic conditions to prepare test samples applicable to the gene amplification method. The strains cultured to prepare test samples are 10 species shown on the first row of Table 8. Human placental DNA was prepared in a concentration of 1 μg/ml and was also subjected to the gene amplification in a similar manner.

The results are shown in Table 8. As in Table 7, the unit of numerical values in the column is a killo base pair. In a part of the bacterial species, the amplified nucleotide fragments considered to be the by-products in gene amplification were detected but each of them a size different from that of the nucleotide fragment deduced from the nucleotide sequence of enterotoxin gene. If these bacteria have the same enterotoxin gene as that of *Clostridium perfringens*, the nucleotide fragment having the same size as the results of Example 1 must be detected. Accordingly, it is evident that the amplified nucleotides derived from these bacteria are not formed by recognizing enterotoxin gene and can thus be readily distinguished over and detected distinctly from *Clostridium perfringens*. By performing agarose gel electrophoresis applied to the examples of the present invention under the aforesaid conditions, differences in size of nucleotides having 5 to 10 base pairs can be distinguished within the range below 100 base pairs and differences in size of nucleotides having 10 to 20 base pairs can be distinguished within the range of from 100 to 500 base pairs. Furthermore, by increasing the accuracy of measurement in size of nucleotide using acrylamide, etc. as gel, reliability in the selective detection is considered to be more enhanced.

TABLE 8

| Strain | Combination of Primer | |
|---|---|---|
|  | (a) + (b) | (a) + (c) |
| *Clostridium perfringens* (ATCC 12917) | 0.73 | 0.60 |
| *Bacillus cereus* (1) | — | 0.20 |
| *Salmonella typhimurium* (2) | 0.60 | — |
| *Staphylococcus aureus* (3) | 0.45 | 0.35 |
| *Escherichia coli* (4) | 0.60 | 0.65 |
| *Vibrio pharahaemolyticus* (5) | 0.45 | — |
| *Campylobacter jejuni* (6) | 0.35 | — |
| *Bacteroides vulgatus* (7) | 0.45 | — |
| *Enterococcus faecalis* (8) | 0.45 | — |
| *Lactobacillus acidophilus* (9) | 0.45 | — |
| *Yersinia enterocolitica* (10) | 0.18 | — |
| Human placenta (11) | — | — |

(1) JCM 2152: Research Institute of Science and Chemistry
(3) JCM 2413: "
(4) JCM 1649: "
(6) JCM 2013: "
(7) JCM 5826: "
(9) JCM 1132: "
(2) IFO 12529: Research Institute of Fermentation
(5) IFO 12711: "
(10) ATCC 9610: American Type Culture Collection
(11) Human placental DNA: manufactured by Onco Co., Ltd.

EXAMPLE 3

With respect to 11 strains of *Clostridium perfringens* used in Example 1, enterotoxin productivity was examined.
Method
Using commercially available kit for detection of enterotoxin (PET-RPLA: DENKA SEIKEN) by the latex agglutination method, enterotoxin activity of each strain of *Clostridium perfringens* was examined in accordance with its manual.
Results
The results are shown in Table 9. The judgement of + or − was made following the standard given in the manual. The results by gene amplification were obtained in a manner similar to Example 1.

TABLE 9

| Strain | Latex Agglutination Method PET-RPLA SEIKEN | Combination of Primer in gene amplification | |
|---|---|---|---|
|  |  | (a) + (b) | (a) + (c) |
| *C. perfringens* (1) | + | 0.73 | 0.60 |
| *C. perfringens* (2) | + | 0.73 | 0.60 |
| *C. perfringens* (3) | + | 0.73 | 0.60 |
| *C. perfringens* (4) | + | 0.73 | 0.60 |
| *C. perfringens* (5) | − | — | — |
| *C. perfringens* (6) | + | 0.73 | 0.60 |
| *C. perfringens* (7) | − | — | — |
| *C. perfringens* (8) | + | 0.73 | 0.60 |
| *C. perfringens* (9) | + | 0.73 | 0.60 |
| *C. perfringens* (10) | + | 0.73 | 0.60 |
| *C. perfringens* (11) | − | 0.30 | — |

Cf. Table 1 with respect to strain numbers (1) through (11) of *Clostridium perfringens* (which is abbreviated as *C. perfringens* in the table) and organization from which the strains were acquired.

As is clear from the results shown in the table, with respect to the strains judged to be + by the latex agglutination method using the commercially available kit, the nucleotide fragment having the accurate size is formed also by the gene amplification method. With respect to the strains judged to be –, either the amplified nucleotide fragment is not formed by the gene amplification, or even though it is formed, the size is greatly different. As described above, the results obtained by the latex agglutination method using the commercially available kit are identical with those obtained by the method of the present invention. This reveals that the enterotoxin productivity of *Clostridium perfringens* can be tested by the presence or absence of enterotoxin gene. Therefore, direct detection of the presence of enterotoxin gene means that *Clostridium perfringens* having enterotoxin productivity is detected. According to the present invention, *Clostridium perfringens* as causative microorganisms of food poisoning can be detected by directly detecting enterotoxin gene of *Clostridium perfringens*. The foregoing results fit the purpose of the present invention.

[Experiment 5: Detection of *Staphylococcus aureus*]

EXAMPLE 1

Preparation of test sample

Using 4 strains shown on the first row in Table 10 as *Staphylococcus aureus*, each strain was inoculated on an appropriate enrichment medium followed by culturing at 37° C. overnight under aerobic conditions. From 1.5 ml of the medium, cells were recovered by centrifugal operation. After washing once with 10 mM Tris-hydrochloride buffer (pH 7.5), the cells were suspended in 0.5 ml of a solution of 1 mg/ml of lysozyme in the buffer to cause bacteriolysis at 37° C. for 10 minutes. The same volume of phenol saturated with the above buffer was added to the bacteriolysis solution and the mixture was thoroughly agitated. After centrifugation, the supernatant was recovered and treated with ethanol to precipitate the nucleic acid component. The precipitate was dissolved in 1 ml of the above buffer and the resulting solution was used as a test sample.

Synthesis of primer

From the nucleotide sequences of enterotoxin B gene for *Staphylococcus aureus* (Ranelli, D. M., et al.; Proc. Natl. Acad. Sci. USA, 82, 5850–5854 (1985)), the sequences (5')d-CCAGATGAGTTGCACAAATCG(3') (a)

(5')d-CACCAAATAGTGACGAGTTA(3') (b)

were selected and oligonucleotides having the same sequences were chemically synthesized. The chemical synthesis was carried out according to the triester method, using DNA synthesizer NS-1, manufactured by Shimadzu Corporation Ltd. The synthesized oligonucleotide fragment was purified using C18 reverse phase column.

Gene amplification

Using 3 μl of the sample solution described above, 16.05 μl of sterile distilled water, 3 μl of buffer for 10-fold reaction, 4.8 μl of dNTP solution, 1.5 μl of primer (a), 1.5 μl of primer (b) and 0.15 μl of thermostable DNA polymerase were added to the sample solution to prepare 30 μl of the reaction solution. To a container charged with the reaction solution, 50 μl of mineral oil (manufactured by SIGMA Co.) was added to form a layer on the reaction solution. The content of each liquid added is shown below.

Buffer for 10-fold reaction: 500 mM KCl, 100 mM Tris-HCl (pH 8.3), 15 mM $MgCl_2$, 0.1% (w/v) gelatin dNTP solution: a mixture of dATP, dCTP, dGTP and dTTP in the final concentration of 1.25 mM each Primers (a) and (b): an aqueous solution of each of the chemically synthesized and purified products (5 ODU/ml)

Thermostable DNA polymerase: Taq DNA polymerase (5 units/ml; manufactured by Perkin Elmer Cetus Co.)

The reaction conditions are as follows:

Thermal denaturation: 94° C., 1 minute
Annealing: 37° C., 1 minute
Polymerization: 60° C., 1 minute The procedure from the thermal denaturation to the polymerization via annealing was made one cycle (time required: 5.7 minutes) and 42 cycles of the procedure were repeated (total time required: about 4 hours). These operations were carried out by programming the reaction conditions described above on DNA Thermal Cycler manufactured by Perkin Elmer Cetus Co., Ltd.

Detection

In order to detect the amplified nucleotide fragment from the reaction solution, agarose gel electrophoresis was performed as follows.

Agarose gel was used in a gel concentration of 2% (w/v). Agarose gel used contained ethidium bromide (0.5 μg/ml ). The electrophoresis was carried out under electric conditions of 100 V in constant voltage for 30 minutes. The procedures and other conditions were the same as those described in Maniatis et al.; Molecular Cloning (1982). In addition to electrophoresis of the reaction solution, a molecular weight marker was also subjected to electrophoresis at the same time. By comparison in relative mobility, the size of the nucleotide fragment was calculated.

Results

As described above, the nucleotide sequences of enterotoxin B gene of *Staphylococcus aureus* were already determined. Therefore, the size of nucleotides amplified by the oligonucleotides of the present invention, namely, the primers, through gene amplification can be deduced. According to the deduction, the size of 486 nucleotides is to be amplified in primers (a) and (b). The numerical values shown in Table 10 show the results obtained by measuring the size of nucleotides amplified by the method described above, wherein the unit is a killo base pair. As is understood from the table, the respective combinations of the primers show numerical values identical with the deduced sizes of nucleotides, indicating that the region targeted by enterotoxin B gene is correctly amplified.

TABLE 10

| Strain | Combination of Primer (a) + (b) |
|---|---|
| *Staphylococcus aureus* (1) | 0.49 |
| *Staphylococcus aureus* (2) | 0.49 |
| *Staphylococcus aureus* (3) | 0.49 |
| *Staphylococcus aureus* (4) | 0.49 |

Strain numbers (1) through (4) of *Staphylococcus aureus* and organizations from which the strains were acquired are shown below.
(1) JCM 2413: Research Institute of Science and Chemistry
(2) JCM 2151: "
(3) JCM 2179: "
(4) JCM 2874: "

EXAMPLE 2

In order to confirm as to if the results obtained in Example 1 are selective to *Staphylococcus aureus*, the results were compared and studied with other species than *Staphylococcus aureus* that could be tested in clinical tests.

The same method as shown in Example 1 was used but with respect to strains (7), (8) and (11), incubation was performed at 40° C. overnight under anaerobic conditions to prepare test samples applicable to the gene amplification method. The strains cultured to prepare test samples are 12 species shown on the first row of Table 11. Human placental DNA was prepared in a concentration of 1 µg/ml and was also subjected to the gene amplification in a similar manner.

The results are shown in Table 11. As in Table 10, the unit of numerical values in the column is a killo base pair. In a part of the bacterial species, the amplified nucleotide fragments considered to be the by-products in gene amplification were detected but each of them has a size different from that of the nucleotide fragment deduced from the nucleotide sequence of enterotoxin gene. If these bacteria have the same enterotoxin gene as that of *Staphylococcus aureus*, the nucleotide fragment having the same size as the results of Example 1 must be detected. Accordingly, it is evident that the amplified nucleotides derived from these bacteria are not formed by recognizing enterotoxin gene and can thus be readily distinguished over and detected distinctly from *Staphylococcus aureus*. By performing agarose gel electrophoresis applied to the examples of the present invention under the aforesaid conditions, differences in size of nucleotides having 5 to 10 base pairs can be distinguished within the range below 100 base pairs and differences in size of nucleotides having 10 to 20 base pairs can be distinguished within the range of from 100 to 500 base pairs. Furthermore, by increasing the accuracy of measurement in size of nucleotide using acrylamide, etc. as gel, reliability in the selective detection is considered to be more enhanced.

TABLE 11

| Strain | Combination of Primer (a) + (b) |
|---|---|
| *Staphylococcus aureus* (JCM 2413) | 0.49 |
| *Staphylococcus epidermidis* (1) | 1.00 |
| *Staphylococcus epidermidis* (2) | 0.65 |
| *Staphylococcus epidermidis* (3) | — |
| *Staphylococcus epidermidis* (4) | 0.40 |
| *Bacillus cereus* (5) | — |
| *Salmonella typhimurium* (6) | 0.40 |
| *Campylobacter jejuni* (7) | — |
| *Escherichia coli* (8) | 0.15 |
| *Vibrio parahaemolyticus* (9) | 0.15 |
| *Clostridium perfringens* (10) | — |
| *Bacteroides vulgatus* (11) | 1.00 |
| *Yersinia enterocolitica* (12) | — |
| Human placenta (13) | — |

Strain numbers (1) through (13) and organizations from which the strains were acquired are shown below.
(1) JCM 2414: Research Institute of Science and Chemistry
(5) JCM 2151: "
(7) JCM 2013: "
(8) JCM 1649: "
(10) JCM 3816: "
(11) JCM 5826: "
(2) IFO 3762: Research Institute of Fermentation
(3) IFO 12993: "
(4) IFO 13389: "
(6) IFO 12529: "
(9) IFO 12771: "
(12) ATCC 9610: American Type Culture Collection
(13) Human placental DNA: manufactured by Onco Co., Ltd.

[Experiment 6: Detection of enterotoxigenic *Escherichia coli*]

EXAMPLE 1

Preparation of test sample

For detection of enterotoxigenic *Escherichia coli*, 40 strains isolated from patients with diarrhea and shown on the first row in Table 12 were used. These strains clinically isolated were acquired, as samples fixed with alkali, from Osaka University, Research Institute of Microorganism Disease and DNA was extracted from the strains. The extraction was carried out as follows. The cells fixed with alkali were again suspended in 0.1N sodium hydroxide to cause bacteriolysis at 60° C. for 15 minutes. The same volume of phenol saturated with the above buffer was added to the bacteriolysis solution and the mixture was thoroughly agitated. After centrifugation, the supernatant was recovered and treated with ethanol to precipitate the nucleic acid component. The precipitate was dissolved in 1 ml of the above buffer and the resulting solution was used as a test sample.

Synthesis of primer

From the nucleotide sequences of LT gene for pathogenic *Escherichia coli* (Yamamoto, T. and Yokota, T., J. Bacteriol., 155, 728–733 (1983)), the sequences (5')d-TTATCAATTTTGGTCTCGGTC(3')    (a)

(5')d-GAACTATGTTCGGAATATCG(3')    b)

were selected and oligonucleotides having the same sequences were chemically synthesized. The chemical synthesis was carried out according to the triester method, using DNA synthesizer NS-1, manufactured by Shimadzu Corporation Ltd. The synthesized oligonucleotide fragment was purified using C18 reverse phase column.

Gene amplification

Using 3 µl of the sample solution described above, 16.05 µl of sterile distilled water, 3 µl of buffer for 10-fold reaction, 4.8 µl of dNTP solution, 1.5 µl of primer (a), 1.5 µl of primer (b) and 0.15 µl of thermostable DNA polymerase were added to the sample solution to prepare 30 µl of the reaction solution. To a container charged with the reaction solution, 50 µl of mineral oil (manufactured by SIGMA Co.) was added to form a layer on the reaction solution. The content of each liquid added is shown below.

Buffer for 10-fold reaction: 500 mM KCl, 100 mM Tris-HCl (pH 8.3), 15 mM $MgCl_2$, 0.1% (w/v) gelatin dNTP solution: a mixture of dATP, dCTP, dGTP and dTTP in the final concentration of 1.25 mM each Primers (a) and (b): an aqueous solution of each of the chemically synthesized and purified products (5 ODU/ml)

Thermostable DNA polymerase: Taq DNA polymerase (5 units/ml; manufactured by Perkin Elmer Cetus Co.)

The reaction conditions are as follows:
Thermal denaturation: 94° C., 1 minute
Annealing: 37° C., 1 minute
Polymerization: 60° C., 1 minute The procedure from the thermal denaturation to the polymerization via annealing was made one cycle (time required: 5.7 minutes) and 42 cycles of the procedure were repeated (total time required: about 4 hours). These operations were carried out by programming the reaction conditions described above on DNA Thermal Cycler manufactured by Perkin Elmer Cetus Co., Ltd.

Detection

In order to detect the amplified nucleotide fragment from the reaction solution, agarose gel electrophoresis was performed as follows.

Agarose gel was used in a gel concentration of 2% (w/v). Agarose gel used contained ethidium bromide (0.5 µg/ml). The electrophoresis was carried out under electric conditions of 100 V in constant voltage for 30 minutes. The procedures and other conditions were the same as those described in Maniatis et al.; Molecular Cloning (1982). In addition to electrophoresis of the reaction solution, a molecular weight marker was also subjected to electrophoresis at the same time. By comparison in relative mobility, the size of the nucleotide fragment detected by ultraviolet rays, etc. in the gel was calculated.

Results

As described above, the nucleotide sequence of LT gene was already determined. Therefore, the size of nucleotides amplified by the oligonucleotides of the present invention, namely, the primers, through gene amplification can be deduced. According to the deduction, the size of 233 nucleotides is to be amplified in primers (a) and (b). The numerical values shown in Table 12 show the results obtained by measuring the size of nucleotides amplified by the method described above. When the size coincided with the deduced size, it was judged to be + and when the size did not coincide, its size was shown. When nothing was detected, it was shown to be −. The results obtained in the present invention are shown by gene amplification. The results shown by Elek are obtained by the prior art method for detection of LT. The results obtained by the Elek method are also shown in the table. As is noted from the table, where gene amplification was caused, the band having a size consistent with that of the deduced nucleotide was detected in the combinations of the respective primers. In addition, a rate of coincidence with the prior art method is extremely high. That is, the results reveal that the region targeted by LT gene is correctly amplified.

TABLE 12

| Strain No. | Elek | PCR* | Strain No. | Elek | PCR* |
| --- | --- | --- | --- | --- | --- |
| 1 | + | + | 21 | − | − |
| 2 | − | − | 22 | − | − |
| 3 | − | − | 23 | − | − |
| 4 | − | − | 24 | + | + |
| 5 | + | + | 25 | + | + |
| 6 | + | + | 26 | + | + |
| 7 | − | − | 27 | + | + |
| 8 | + | + | 28 | + | − |
| 9 | + | + | 29 | − | − |
| 10 | + | + | 30 | − | − |
| 11 | − | − | 31 | − | − |
| 12 | − | − | 32 | − | − |
| 13 | − | − | 33 | − | − |
| 14 | + | + | 34 | − | − |
| 15 | + | + | 35 | + | + |
| 16 | + | − | 36 | + | + |
| 17 | + | + | 37 | − | − |
| 18 | + | + | 38 | − | − |
| 19 | − | − | 39 | − | − |
| 20 | − | − | 40 | − | − |

*PCR: gene amplification

Strain numbers (1) through (40) of enterotoxigenic *Escherichia coli* were acquired from Osaka University, Research Institute of Microorganism Disease.

EXAMPLE 2

In order to confirm as to if the results obtained in Example 1 are selective to enterotoxigenic *Escherichia coli*, the results were compared and studied with other species than enterotoxigenic *Escherichia coli* that could be tested in clinical tests.

The same method as shown in Example 1 was used but with respect to *Campylobacter jejuni*, *Clostridium perfringens*, *Bacteroides vulgatus*, *Enterococcus faecalis* and *Lactobacillus acidophilus*, incubation was performed at 37 ° C. overnight under anaerobic conditions to prepare test samples applicable to the gene amplification method. The strains cultured to prepare test samples are 17 species shown on the first row of Table 13. Human placental DNA was prepared in a concentration of 1 μg/ml and was also subjected to the gene amplification in a similar manner. The results are shown in Table 13, wherein the unit of numerical values in the column is a killo base pair. In *Yersinia enterocolitica*, the amplified nucleotide fragment considered to be the by-product in gene amplification was detected but it has the size different from that of the nucleotide fragment deduced from the nucleotide sequence of LT gene. If these bacteria have the same LT gene as that of enterotoxigenic *Escherichia coli*, the nucleotide fragment having the same size as the results of Example 1 must be detected. Accordingly, it is evident that the amplified nucleotides derived from this bacteria are not formed by recognizing LT gene and can thus be readily distinguished over and detected distinctly from enterotoxigenic *Escherichia coli*. On the other hand, it was revealed that there was no cross reaction with *Vibrio cholerae* at all in the present invention. As has been described above, enterotoxin of *Vibrio cholerae* and LT had a common antigen so that they could not be distinguished from each other even by immunological technique. However, according to the present invention, only LT clearly reacts and it is thus considered that its reliability is much higher than in the prior art method. By performing agarose gel electrophoresis applied to the examples of the present invention under the aforesaid conditions, differences in size of nucleotides having 5 to 10 base pairs can be distinguished within the range below 100 base pairs and differences in size of nucleotides having 10 to 20 base pairs can be distinguished within the range of from 100 to 500 base pairs. Furthermore, by increasing the accuracy of measurement in size of nucleotide using acrylamide, etc. as gel, reliability in the selective detection is considered to be more enhanced.

TABLE 13

| Strain | Abbreviation in Preserving Organization and Strain Number | |
| --- | --- | --- |
| *Bacillus cereus* | JCM 2152 | — |
| *Salmonella typhimurium* | IFO 12529 | — |
| *Campylobacter jejuni* | JCM 2013 | — |
| *Escherichia coli* | JCM 1649 | — |
| *Staphylococcus aureus* | JCM 2413 | — |
| *Vibrio pharahaemolyticus* | IFO 12711 | — |
| *Clostridium perfringens* | ATCC 12917 | — |
| *Bacteroides vulgatus* | JCM 5826 | — |
| *Yersinia enterocolitica* | ATCC 9610 | 0.8 |
| *Vibrio cholerae* | ATCC 9458 | — |
| *Vibrio cholerae* | ATCC 9459 | — |
| *Vibrio cholerae* | ATCC 25872 | — |
| *Shigella dysenteriae* | ATCC 9361 | — |
| *Shigella flexneri* | ATCC 29903 | — |
| *Shigella sonnei* | ATCC 29930 | — |
| *Enterococcus faecalis* | JCM 5803 | — |
| *Lactobacillus acidophilus* | JCM 1132 | — |
| Human placenta | | — |

[Experiment 7: Detection of *Campylobacter jejuni*]

EXAMPLE 1

Preparation of test sample Using 8 strains of *Campylobacter jejuni* shown in Table 14, test samples were prepared by the following method. *Campylobacter jejuni* was inoculated on GAM medium in a closed container followed by culturing for 2 to 3 days in a gaseous atmosphere using a gas generator (manufactured by BBL Co., Ltd.) for Campylobacter. After the cells recovered were washed with an appropriate inorganic salt buffer, lysozyme (final concentration of 1 mg/ml) was added to the cells in the buffer under ice cooling to cause bacteriolysis. Next, SDS (final concentration of 1%) and protease K (final concentration of 100 μg/ml) were added and the resulting mixture was heated at 50° C. for 30 minutes. The system was again put under ice cooling. After treatment with phenol and precipitation with ethanol, the precipitates were recovered and dissolved in 10 mM Tris-hydrochloride buffer (pH 7.5). The resulting solution was used as a test sample. An amount of nucleic acid was calculated from absorbancy at a wavelength of 260 nm was 1 μg/ml.

Preparation of primer

Oligonucleotides having the sequences (5')d-AATAATCTGAATCCGATGGT(3')     (a)

(5')d-ATCAGACCATCACCCTTATC(3')     (b)

were chemically synthesized. The chemical synthesis was carried out according to the triester method, using DNA synthesizer NS-1, manufactured by Shimadzu Corporation Ltd. The synthesized oligonucleotide fragment was purified using C18 reverse phase column.

Gene amplification

Using 3 μl of the sample solution described above, 16.05 μl of sterile distilled water, 3 μl of buffer for 10-fold reaction, 4.8 μl of dNTP solution, 1.5 μl of primer (a), 1.5 μl of primer (b) and 0.15 μl of thermostable DNA polymerase were added to the sample solution to prepare 30 μl of the reaction solution. To a container charged with the reaction solution, 50 μl of mineral oil (manufactured by SIGMA Co.) was added to form a layer on the reaction solution. The content of each liquid added is shown below.

Buffer for 10-fold reaction: 500 mM KCl, 100 mM Tris-HCl (pH 8.3), 15 mM $MgCl_2$, 0.1% (w/v) gelatin dNTP solution: a mixture of dATP, dCTP, dGTP and dTTP in the final concentration of 1.25 mM each Primers (a) and (b): an aqueous solution of each of the chemically synthesized and purified products (5 ODU/ml)

Thermostable DNA polymerase: Taq DNA polymerase (5 units/ml; manufactured by Perkin Elmer Cetus Co.)

The reaction conditions are as follows:
Thermal denaturation: 94° C., 1 minute
Annealing: 37° C., 1 minute
Polymerization: 60° C., 1 minute The procedure from the thermal denaturation to the polymerization via annealing was made one cycle (time required: 5.7 minutes) and 42 cycles of the procedure were repeated (total time required: about 4 hours). These operations were carried out by programming the reaction conditions described above on DNA Thermal Cycler manufactured by Perkin Elmer Cetus Co., Ltd.

Detection

In order to detect the amplified nucleotide fragment from the reaction solution, agarose gel electrophoresis was performed as follows.

Agarose gel was used in a gel concentration of 2% (w/v). Agarose gel used contained ethidium bromide (0.5 μg/ml). The electrophoresis was carried out under electric conditions of 100 V in constant voltage for 30 minutes. The procedures and other conditions were the same as those described in Maniatis et al.; Molecular Cloning (1982). In addition to electrophoresis of the reaction solution, a molecular weight marker was also subjected to electrophoresis at the same time. By comparison in relative mobility, the size of the nucleotide fragment detected by ultraviolet rays, etc. in the gel was calculated.

Results

With respect to *Campylobacter jejuni*, the amplified DNA fragment of 1.2 killo base pairs was formed. This is a phenomenon common to all of the 8 strains and strongly suggests that the combination of the primers would be effective for selective detection of *Campylobacter jejuni*.

TABLE 14

| Strain | Number Allotted by Organization for Distribution | |
| --- | --- | --- |
| Campylobacter jejuni | JCM 2013 | 1.2 |
| Campylobacter jejuni | ATCC 33250 | 1.2 |
| Campylobacter jejuni | ATCC 33251 | 1.2 |
| Campylobacter jejuni | ATCC 33252 | 1.2 |
| Campylobacter jejuni | ATCC 33253 | 1.2 |
| Campylobacter jejuni | ATCC 33291 | 1.2 |
| Campylobacter jejuni | ATCC 33292 | 1.2 |
| Campylobacter jejuni | ATCC 33560 | 1.2 |

ATCC: American Type Culture Collection
JCM: Research Institute of Science and Chemistry, Institution of Microorganism Strain Preservation

EXAMPLE 2

In order to confirm as to if the results obtained in Example 1 are selective to *Campylobacter jejuni*, the results were compared and studied with other species than *Campylobacter jejuni* that could be tested in clinical tests.

The same method as shown in Example 1 was used but with respect to *Clostridium perfringens*, *Bacteroides vulgatus*, *Enterococcus faecalis* and *Lactobacillus acidophilus*, incubation was performed at 37° C. overnight under anaerobic conditions to prepare test samples applicable to the gene amplification method. The strains cultured to prepare test samples are 16 species shown on the first row of Table 15. Human placental DNA was prepared in a concentration of 1 μg/ml and was also subjected to the gene amplification in a similar manner. The results are shown in Table 15, wherein numerical values in the column indicate the size of amplified DNA and their unit is a killo base pair. If the bacteria has the same nucleotide sequence in the chromosomal gene as that of *Campylobacter jejuni*, the nucleotide fragment having the same size (1.2 killo base pair) as the results of Example 1 must be detected. Accordingly, it is evident that the amplified nucleotides derived from the bacteria can be readily distinguished over and detected distinctly from those formed by recognizing the chromosomal gene of *Campylobacter jejuni*. By performing agarose gel electrophoresis applied to the examples of the present invention under the aforesaid conditions, differences in size of nucleotides having 5 to 10 base pairs can be distinguished within the range below 100 base pairs and differences in size of nucleotides having 10 to 20 base pairs can be distinguished within the range of from 100 to 500 base pairs. Furthermore, by increasing the accuracy of measurement in size of nucleotide using acrylamide, etc. as gel, reliability in the selective detection is considered to be more enhanced.

TABLE 15

| Strain | Abbreviation in Preserving Organization and Strain Number | |
| --- | --- | --- |
| Campylobacter jejuni | JCM 2013 | 1.2 |
| Campylobacter coli | JCM 2529 | — |

TABLE 15-continued

| Strain | Abbreviation in Preserving Organization and Strain Number | |
|---|---|---|
| Campylobacter fetus | JCM 2527 | — |
| Campylobacter laridis | JCM 2530 | 0.75 |
| Campylobacter fecalis | ATCC 33709 | 0.75 |
| Campylobacter fecalis | ATCC 33709 | 0.10 |
| Bacillus cereus | JCM 2152 | 2.0 |
| Salmonella typhimurium | IFO 12529 | — |
| Escherichia coli | JCM 1649 | 0.35 |
| Staphylococcus aureus | JCM 2413 | 1.5 |
| Vibrio pharahaemolyticus | IFO 12711 | — |
| Clostridium perfringens | ATCC 12917 | 0.15 |
| Bacteroides vulgatus | JCM 5826 | — |
| Yersinia enterocolitica | ATCC 9610 | — |
| Enterococcus faecalis | JCM 5803 | 0.40 |
| Lactobacillus acidophilus | JCM 1132 | 0.40 |
| Human placenta | | 0.45 |

[Experiment 8: Detection of enterotoxigenic *Escherichia coli* capable of producing thermostable toxin (ST)]

EXAMPLE 1

Preparation of test sample

For survey of enterotoxigenic *Escherichia coli*, 40 strains isolated from patients with diarrhea and shown on the first row in Table 16 were used. These strains clinically isolated were acquired, as samples fixed with alkali, from Osaka University, Research Institute of Microorganism Disease and DNA was extracted from the strains. The extraction was carried out as follows. The cells fixed with alkali were again suspended in 0.1N sodium hydroxide to cause bacteriolysis at 60° C. for 15 minutes. The same volume of phenol saturated with the above buffer was added to the bacteriolysis solution and the mixture was thoroughly agitated. After centrifugation, the supernatant was recovered and treated with ethanol to precipitate the nucleic acid component. The precipitate was dissolved in 1 ml of the above buffer and the resulting solution was used as a test sample.

Synthesis of primer

From the nucleotide sequences of ST gene for enterotoxigenic *Escherichia coli* (Moseley, S. L., et al., Infect. Immun., 39, 1167–1174 (1983)), the sequences (5')d-TAATAGCACCCGGTACAAGC(3')     (a)

(5')d-ATAAAAGTGGTCCTGAAAGC(3')     (b)

were selected and oligonucleotides having the same sequences were chemically synthesized. The chemical synthesis was carried out according to the triester method, using DNA synthesizer NS-1, manufactured by Shimadzu Corporation Ltd. The synthesized oligonucleotide fragment was purified using C18 reverse phase column.

Gene amplification

Using 3 μl of the sample solution described above, 16.05 μl of sterile distilled water, 3 μl of buffer for 10-fold reaction, 4.8 μl of dNTP solution, 1.5 μl of primer (1), 1.5 μl of primer (2) and 0.15 μl of thermostable DNA polymerase were added to the sample solution to prepare 30 μl of the reaction solution. To a container charged with the reaction solution, 50 μl of mineral oil (manufactured by SIGMA Co.) was added to form a layer on the reaction solution. The content of each liquid added is shown below.

Buffer for 10-fold reaction: 500 mM KCl, 100 mM Tris-HCl (pH 8.3), 15 mM $MgCl_2$, 0.1% (w/v) gelatin dNTP solution: a mixture of dATP, dCTP, dGTP and dTTP in the final concentration of 1.25 mM each Primers (1) and (2): an aqueous solution of each of the chemically synthesized and purified products (5 ODU/ml)

Thermostable DNA polymerase: Taq DNA polymerase (5 units/ml; manufactured by Perkin Elmer Cetus Co.)

The reaction conditions are as follows:

Thermal denaturation: 94° C., 1 minute

Annealing: 37° C., 1 minute

Polymerization: 60° C., 1 minute

The procedure from the thermal denaturation to the polymerization via annealing was made one cycle (time required: 5.7 minutes) and 42 cycles of the procedure were repeated (total time required: about 4 hours). These operations were carried out by programming the reaction conditions described above on DNA Thermal Cycler manufactured by Perkin Elmer Cetus Co., Ltd.

Detection

In order to detect the amplified nucleotide fragment from the reaction solution, agarose gel electrophoresis was performed as follows.

Agarose gel was used in a gel concentration of 2% (w/v). Agarose gel used contained ethidium bromide (0.5 μg/ml). The electrophoresis was carried out under electric conditions of 100 V in constant voltage for 30 minutes. The procedures and other conditions were the same as those described in Maniatis et al.; Molecular Cloning (1982). In addition to electrophoresis of the reaction solution, a molecular weight marker was also subjected to electrophoresis at the same time. By comparison in relative mobility, the size of the nucleotide fragment detected by ultraviolet rays, etc. in the gel was calculated.

Results

As described above, the nucleotide sequence of ST gene was already determined. Therefore, the size of nucleotides amplified by the oligonucleotides of the present invention, namely, the primers, through gene amplification can be deduced. According to the deduction, the size of 80 nucleotides is to be amplified in primers (1) and (2). The numerical values shown in Table 16 show the results obtained by measuring the size of nucleotides amplified by the method described above (gene amplification). When the size coincided with the deduced size, it was judged to be + and when the size did not coincide, its size was shown. When nothing was detected, it was shown to be —. The results obtained in the present invention are shown by gene amplification. The results shown by SM are obtained by the aforesaid lactating mouse method. As is noted from the table, with respect to the strains which reacted also with any combination of the primers, their size coincided with that of the deduced nucleotide and is closely related also to the results with ST. Accordingly, the results strongly suggest that the region targeted by ST gene is correctly amplified, indicating effectiveness for detection of ST-producing enterotoxigenic *Escherichia coli*.

TABLE 13

| Strain No. | SM | PCR* | Strain No. | SM | PCR* |
|---|---|---|---|---|---|
| 1 | + | + | 21 | + | + |
| 2 | + | + | 22 | + | + |
| 3 | + | + | 23 | — | + |
| 4 | — | — | 24 | + | + |
| 5 | — | — | 25 | — | — |
| 6 | + | + | 26 | — | — |
| 7 | — | — | 27 | — | — |
| 8 | + | + | 28 | + | + |
| 9 | — | — | 29 | + | + |

TABLE 13-continued

| Strain No. | SM | PCR* | Strain No. | SM | PCR* |
|---|---|---|---|---|---|
| 10 | + | − | 30 | + | + |
| 11 | + | − | 31 | − | − |
| 12 | − | − | 32 | − | − |
| 13 | + | + | 33 | + | − |
| 14 | + | − | 34 | + | − |
| 15 | − | − | 35 | − | − |
| 16 | + | − | 36 | − | − |
| 17 | − | − | 37 | − | − |
| 18 | − | − | 38 | − | − |
| 19 | − | − | 39 | + | + |
| 20 | − | − | 40 | + | + |

*PCR gene amplification

Strain numbers (1) through (40) of enterotoxigenic *Escherichia coli* were acquired from Osaka University, Research Institute of Microorganism Disease.

EXAMPLE 2

In order to confirm as to if the results obtained in Example 1 is selective to enterotoxigenic *Escherichia coli*, the results were compared and studied with other species than enterotoxigenic *Escherichia coli* that could be tested in clinical tests.

The same method as shown in Example 1 was used but with respect to *Campylobacter jejuni, Clostridium perfringens, Bacteroides vulgatus, Enterococcus faecalis* and *Lactobacillus acidophilus*, incubation was performed at 37° C. overnight under anaerobic conditions to prepare test samples applicable to the gene amplification method. The strains cultured to prepare test samples are 12 species shown on the first row of Table 17. Human placental DNA was prepared in a concentration of 1 µg/ml and was also subjected to the gene amplification in a similar manner. The results are shown in Table 17, wherein unit of numerical values in the column is killo base pair. If these bacteria have the same ST gene as that of enterotoxigenic *Escherichia coli*, the nucleotide fragment having the same size as the results of Example 1 must be detected. Accordingly, it is evident that the amplified nucleotides derived from this bacteria are not formed by recognizing ST gene and can thus be readily distinguished over and detected distinctly from enterotoxigenic *Escherichia coli*. By performing agarose gel electrophoresis applied to the examples of the present invention under the aforesaid conditions, differences in size of nucleotides having 5 to 10 base pairs can be distinguished within the range below 100 base pairs and differences in size of nucleotides having 10 to 20 base pairs can be distinguished within the range of from 100 to 500 base pairs. Furthermore, by increasing the accuracy of measurement in size of nucleotide using acrylamide, etc. as gel, reliability in the selective detection is considered to be more enhanced.

TABLE 17

| Strain | Abbreviation in Preserving Organization and Strain Number | |
|---|---|---|
| *Bacillus cereus* | JCM 2152 | 0.20 |
| *Salmonella typhimurium* | IFO 12529 | — |
| *Campylobacter jejuni* | JCM 2013 | — |
| *Escherichia coli* | JCM 1649 | — |
| *Staphylococcus aureus* | JCM 2413 | — |
| *Vibrio pharahaemolyticus* | IFO 12711 | — |
| *Clostridium perfringens* | ATCC 12917 | — |
| *Bacteroides vulgatus* | JCM 5826 | 0.20 |

TABLE 17-continued

| Strain | Abbreviation in Preserving Organization and Strain Number | |
|---|---|---|
| *Yersinia enterocolitica* | ATCC 9610 | — |
| *Vibrio cholerae* | ATCC 9458 | 0.60 |
| *Vibrio cholerae* | ATCC 9459 | — |
| *Vibrio cholerae* | ATCC 25872 | 0.60 |
| Human placenta | | 0.10 |

[Experiment 9: Detection of *Salmonella typhimurium*]

EXAMPLE 1

Preparation of test sample

Using 8 strains shown on the first row in Table 18 as *Salmonella typhimurium*, each strain was inoculated on an appropriate enrichment medium followed by culturing at 37° C. overnight under aerobic conditions. From 1.5 ml of the medium, cells were recovered by centrifugal operation. After washing once with 10 mM Tris-hydrochloride buffer (pH 7.5), the cells were suspended in 0.5 ml of a solution of 1 mg/ml of lysozyme in the buffer to cause bacteriolysis at 37° C. for 10 minutes. The same volume of phenol saturated with the above buffer was added to the bacteriolysis solution and the mixture was thoroughly agitated. After centrifugation, the supernatant was recovered and treated with ethanol to precipitate the nucleic acid component. The precipitate was dissolved in 1 ml of the above buffer and the resulting solution was used as a test sample.

Synthesis of primer

From the nucleotide sequences of flagellin gene for *Salmonella typhimurium* (Zeig, J. and Simon, M.; Proc. Natl. Acad. Sci. USA, 77, 4196–4200 (1980)), the sequences (5')d-GCGATACTCTTGTCGTCTGG(3')   (a)

(5')d-ATAGCTAATTGCTGCCGAGG(3')   (b)

were selected and oligonucleotides having the same sequences were chemically synthesized. The chemical synthesis was carried out according to the triester method, using DNA synthesizer NS-1, manufactured by Shimadzu Corporation Ltd. The synthesized oligonucleotide fragment was purified using C18 reverse phase column.

Gene amplification

Using 3 µl of the sample solution described above, 16.05 µl of sterile distilled water, 3 µl of buffer for 10-fold reaction, 4.8 µl of dNTP solution, 1.5 µl of primer (1), 1.5 µl of primer (2) and 0.15 µl of thermostable DNA polymerase were added to the sample solution to prepare 30 µl of the reaction solution. To a container charged with the reaction solution, 50 µl of mineral oil (manufactured by SIGMA Co.) was added to form a layer on the reaction solution. The content of each liquid added is shown below.

Buffer for 10-fold reaction: 500 mM KCl, 100 mM Tris-HCl (pH 8.3), 15 mM MgCl$_2$, 0.1% (w/v) gelatin dNTP solution: a mixture of dATP, dCTP, dGTP and dTTP in the final concentration of 1.25 mM each Primers (1) and (2): an aqueous solution of each of the chemically synthesized and purified products (5 ODU/ml)

As the combination of primers, the sequences ((a), (b)) shown in claim 27 were used.

Thermostable DNA polymerase: Taq DNA polymerase (5 units/ml; manufactured by Perkin Elmer Cetus Co.)

The reaction conditions are as follows:
  Thermal denaturation: 94° C., 1 minute
  Annealing: 37° C. 1 minute
  Polymerization: 60° C., 1 minute The procedure from the thermal denaturation to the polymerization via annealing was made one cycle (time required: 5.7 minutes) and 42 cycles of the procedure were repeated (total time required: about 4 hours). These operations were carried out by programming the reaction conditions described above on DNA Thermal Cycler manufactured by Perkin Elmer Cetus Co., Ltd.

Detection

In order to detect the amplified nucleotide fragment from the reaction solution, agarose gel electrophoresis was performed as follows.

Agarose gel was used in a gel concentration of 2% (w/v). Agarose gel used contained ethidium bromide (0.5 µg/ml). The electrophoresis was carried out under electric conditions of 100 V in constant voltage for 30 minutes. The procedures and other conditions were the same as those described in Maniatis et al.; Molecular Cloning (1982). In addition to electrophoresis of the reaction solution, a molecular weight marker was also subjected to electrophoresis at the same time. By comparison in relative mobility, the size of the nucleotide fragment was calculated.

Results

As described above, the nucleotide sequences of flagellin gene of *Salmonella typhimurium* were already determined. Therefore, the size of nucleotides amplified by the oligonucleotides of the present invention, namely, the primers, through gene amplification can be deduced. According to the deduction, the size of 334 nucleotides are to be amplified. The numerical values shown in Table 18 show the results obtained by measuring the size of nucleotides amplified by the method described above, wherein the unit is a killo base pair.

As is understood from the table, the respective combinations of the primers show numerical values consistent with the deduced sizes of nucleotides, indicating that the region targeted by flagellin gene is correctly amplified.

TABLE 18

| Strain | |
|---|---|
| *Salmonella typhimurium* (1) | 0.33 |
| *Salmonella typhimurium* (2) | 0.33 |
| *Salmonella typhimurium* (3) | 0.33 |
| *Salmonella typhimurium* (4) | 0.33 |
| *Salmonella typhimurium* (5) | 0.33 |
| *Salmonella typhimurium* (6) | 0.33 |
| *Salmonella typhimurium* (7) | 0.33 |
| *Salmonella typhimurium* (8) | 0.33 |

Strain numbers (1) through (8) of *Salmonella typhimurium* and organizations from which the strains were acquired are shown below.
(1) IFO 12529: Research Institute of Fermentation
(2) IFO 13425: "
(3) IFO 14193: "
(4) IFO 14194: "
(5) IFO 14209: "
(6) IFO 14210: "
(7) IFO 14211: "
(8) IFO 14212: "

EXAMPLE 2

In order to confirm as to if the results obtained in Example 1 is selective to *Salmonella typhimurium*, the results were compared and studied with other species than *Salmonella typhimurium* that could be tested in clinical tests.

The same method as shown in Example 1 was used but with respect to strains (8), (12) and (17), incubation was performed at 40° C. overnight under anaerobic conditions to prepare test samples applicable to the gene amplification method. The strains cultured to prepare test samples are 18 species shown on the first row of Table 19. Human placental DNA was prepared in a concentration of 1 µg/ml and was also subjected to the gene amplification in a similar manner.

The results are shown in Table 19. As in Table 18, the unit of numerical values in the column is a killo base pair. In a part of the bacterial species, the amplified nucleotide fragments considered to be the by-products in gene amplification were detected but each of them has the size different from that of the nucleotide fragment deduced from the nucleotide sequence of flagellin gene. If these bacteria have the same flagellin gene as that of *Salmonella typhimurium*, the nucleotide fragment having the same size as the results of Example 1 must be detected. Accordingly, it is evident that the amplified nucleotides derived from these bacteria are not formed by recognizing flagellin gene and can thus be readily distinguished over and detected distinctly from *Salmonella typhimurium*. By performing agarose gel electrophoresis applied to the examples of the present invention under the aforesaid conditions, differences in size of nucleotides having 5 to 10 base pairs can be distinguished within the range below 100 base pairs and differences in size of nucleotides having 10 to 20 base pairs can be distinguished within the range of from 100 to 500 base pairs. Furthermore, by increasing the accuracy of measurement in size of nucleotide using acrylamide, etc. as gel, reliability in the selective detection is considered to be more enhanced.

TABLE 19

| Strain | |
|---|---|
| *Salmonella typhimurium* (IFO 12529) | 0.33 |
| *Salmonella enteritidis* (1) | — |
| *Salmonella gallinarum* (2) | — |
| *Salmonella blockeley* (3) | — |
| *Salmonella derby* (4) | — |
| *Salmonella infantis* (5) | — |
| *Salmonella montevideo* (6) | — |
| *Bacillus cereus* (7) | — |
| *Campylobacter jejuni* (8) | — |
| *Escherichia coli* (9) | — |
| *Vibrio parahaemolyticus* (10) | — |
| *Staphylococcus aureus* (11) | — |
| *Clostridium perfringens* (12) | — |
| *Shigella dysenteriae* (13) | — |
| *Shigella flexneri* (14) | — |
| *Shigella sonnei* (15) | 0.75 |
| *Yersinia enterocolitica* (16) | 0.78 |
| *Bacteroides vulgatus* (17) | 0.45 |
| Human placenta (18) | — |

(1) IFO 3313, (2) IFO 3163, (3) NIAH 1197, (4) NIAH 1199, (5) NIAH 1218, (6) NIAH 1221, (7) JCM 2152, (8) JCM 2013, (9) JCM 1469, (10) IFO 12711, (11) JCM 2413, (12) ATCC 12917, (13) ATCC 9361, (14) ATCC 29903, (15) ATCC 29930, (16) ATCC 9610, (17) JCM 5826
(7), (8), (9), (11), (17) . . . Research Institute of Science and Chemistry
(1), (2), (10) . . . Research Institute of Fermentation
(3), (4), (5), (6) . . . National Institute of Animal Health of the Ministry of Agriculture, Forestry and Fisheries
(12), (13), (14), (15), (16) . . . American Type Culture Collection
(18) Human placental DNA: manufactured by Onco Co., Ltd.

According to the present invention, high detection sensitivity by gene amplification and high sensitivity due to the reaction controlled by two or more primers can be obtained in detection for causative microorganisms of food poisoning. Because of high detection sensitivity, large quantities of test samples are not required and pretreatment of test samples can be simplified. In addition, a reaction time is shortened and detection can be made merely by simple equipment. The operation is easy so that a time period required for identification can be greatly shortened. As demonstrated in the foregoing examples, it takes 4 hours for the reaction and 30 minutes for the operations for detection. Furthermore, by using agarose gel electrophoresis and nucleic acid staining with ethidium bromide, detection can be made without labeling the primers, etc. and the size of the nucleic acid can be confirmed. Thus, reliability of the results is high.

What is claimed is:

1. A method that tests for a causative bacterial species in food poisoning comprising the sequential steps of:
   a. thermally or pH denaturing a nucleic acid test sample;
   b. reacting the sample with at least one pair of oligonucleotide primers, each primer of which will hybridize to a gene on opposite strands of DNA from the causative bacterial species, wherein for Bacillus cereus the at least one pair of oligonucleotide primers is selected from the group consisting of:
   (5')d-GGTTTAAGTATTACAAGCC(3') and (5')d-GCATATACACCTAATCGAGC(3'),
   (5')d-GGTTTAAGTATTACAAGCC(3') and (5')d-CCACTAAGTCTTCTTTCG(3'),
   (5')d-TTCTGTATGCCCTTTCCCTG(3') and (5')d-ATTTCAGAAGCGCGTAACGG(3'),
   for Salmonella the at least one pair is selected from the group consisting of:
   (5')d-GGCGAGCAGTTTGTCTGTC(3') and (5')d-TACCGCCATACGTCTGAGC(3'),
   (5')d-GGCGAGCAGTTTGTCTGTC(3') and (5')d-GTTTCGCCTGGCTGATACG(3'),
   for Clostridium perfringens the at least one pair is selected from the group consisting of:
   (5')d-AATACATATTGTCCTGCATC(3') and (5')d-GTAATAGATAAAGGAGATGG(3'),
   (5')d-AATACATATTGTCCTGCATC(3') and (5')d-GTAGTAGGATTTATACAAGC(3'),
   for Campylobacter jejuni the pair is:
   (5')d-AATAATCTGAATCCGATGGT(3') and (5')d-ATCAGACCATCACCCTTATC(3'),
   and
   for Salmonella typhimurium the pair is:
   (5')d-GCGATACTCTTGTCGTCTGG(3') and (5')d-ATAGCTAATTGCTGCCGAGG(3');
   c. reacting the sample with a mixture of dATP, dCTP, dGTP, and dTTP, in order to extend the hybridized primers;
   d. heating or modifying the pH of the sample, in order to free the extended primers to form complementary single strand DNA fragments;
   e. reacting the sample with the at least one pair of oligonucleotide primers, each primer of which will hybridize with one of the corresponding single strand DNA fragments;
   f. reacting the sample with a mixture of dATP, dCTP, dGTP, and dTTP, in order to extend the primers that hybridized to the complementary single strand DNA fragment and, thereby, form a double strand DNA fragment;
   g. repeating steps (d)–(f) a sufficient number of times to amplify the double strand DNA fragment to effect a detectable amount; and
   h. subjecting the sample to testing to detect whether the double strand DNA fragment is present, which would confirm the causative bacterial species.

2. A method as defined in claim 1 wherein said bacterial species of food poisoning is Bacillus cereus and said specific gene of the bacteria is β-lactamase gene of Bacillus cereus.

3. A method as defined in claim 1 wherein detection of said specific fragment is carried out by agarose gel electrophoresis and staining of nucleic acid with ethidium bromide.

4. A reagent for testing Bacillus cereus which is a synthetic oligonucleotide, targeting β-lactamase gene of Bacillus cereus, and being complementary to the sequence of said β-lactamase gene, said synthetic oligonucleotide being composed of the following group of sequences;

| | |
|---|---|
| (5')d-GGTTTAAGTATTACAAGCC(3') | (a) |
| (5')d-GCATATACACCTAATCGAGC(3') | (b) |
| (5')d-CCACTAAGTCTTCTTTCG(3') | (c) |
| (5')d-TTCTGTATGCCCTTTCCCTG(3') | (d) |
| (5')d-ATTTCAGAAGCGCGTAACGG(3') | (e) | or the corresponding complementary sequence.

5. A method as defined in claim 2 wherein the at least one pair of oligonucleotide primers are (5')d-GGTTTAAGTATTACAAGCC(3') and (5')d-GCATATACACCTAATCGAGC(3'), (5')d-GGTTTAAGTATTACAAGCC(3') and (5')d-CCACTAAGTCTTCTTTCG (3'), and (5')d-TTCTGTATGCCCTTTCCCTG(3') and (5')d-ATTTCAGAAGCGCGTAACGG(3'), whose sequences are complementary to the sequence of the gene according to claim 2.

* * * * *